United States Patent
Lerestif et al.

(10) Patent No.: US 7,064,200 B2
(45) Date of Patent: Jun. 20, 2006

(54) PROCESS FOR THE SYNTHESIS OF 1,3,4,5-TETRAHYDRO-2H-3-BENZAZEPIN-2-ONE COMPOUNDS, AND APPLICATION IN THE SYNTHESIS OF IVABRADINE AND ADDITION SALTS THEREOF WITH A PHARMACEUTICALLY ACCEPTABLE ACID

(75) Inventors: Jean-Michel Lerestif, Yvetot (FR);
Jean-Pierre Lecouve, Le Havre (FR);
Jean-Claude Souvie, Le Havre (FR);
Daniel Brigot, Sainte-Marie-des-Champs (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 11/060,043

(22) Filed: Feb. 17, 2005

(65) Prior Publication Data
US 2005/0228178 A1    Oct. 13, 2005

(30) Foreign Application Priority Data
Apr. 13, 2004   (FR) ................... 04 03828

(51) Int. Cl.
*C07D 491/56*    (2006.01)
(52) U.S. Cl. .................................... 540/523
(58) Field of Classification Search .......... 540/523
See application file for complete search history.

(56) References Cited

FOREIGN PATENT DOCUMENTS

| EP | 0204349 | 12/1986 |
|---|---|---|
| EP | 0534859 | 3/2003 |

OTHER PUBLICATIONS

*French Search Report for French Application No. 04.03828,* Dec. 16, 2004.
*European Search Report for European Application No. 05290383,* Jul. 7, 2005.
Bomhard, et al., *J. Med. Chem.*, 1991, 34, 942-947.
Reiffen, et al., *J. Med. Chem.*, 1990, 33, 1496-1504.

*Primary Examiner*—Bruck Kifle
(74) *Attorney, Agent, or Firm*—Hueschen and Sage

(57) ABSTRACT

Process for the synthesis of compounds of formula (I):

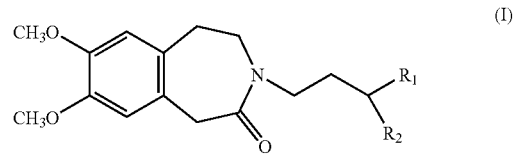

(I)

wherein $R_1$ and $R_2$, which may be the same or different, each represent a linear or branched ($C_1$–$C_8$)alkoxy group or form, together with the carbon atom carrying them, a 1,3-dioxane, 1,3-dioxolane or 1,3-dioxepane ring.

Application in the synthesis of ivabradine, addition salts thereof with a pharmaceutically acceptable acid, and hydrates thereof.

11 Claims, No Drawings

PROCESS FOR THE SYNTHESIS OF 1,3,4,5-TETRAHYDRO-2H-3-BENZAZEPIN-2-ONE COMPOUNDS, AND APPLICATION IN THE SYNTHESIS OF IVABRADINE AND ADDITION SALTS THEREOF WITH A PHARMACEUTICALLY ACCEPTABLE ACID

The present invention relates to a process for the synthesis of 1,3,4,5-tetrahydro-2H-3-benzazepin-2-one compounds, and to the application thereof in the synthesis of ivabradine and addition salts thereof with a pharmaceutically acceptable acid.

More specifically, the present invention relates to a process for the synthesis of compounds of formula (I):

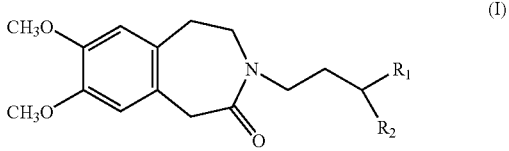

wherein $R_1$ and $R_2$, which may be the same or different, each represent a linear or branched ($C_1$–$C_8$)alkoxy group or form, together with the carbon atom carrying them, a 1,3 dioxane, 1,3-dioxolane or 1,3-dioxepane ring.

BACKGROUND OF THE INVENTION

The compounds of formula (I) obtained according to the process of the invention are useful in the synthesis of ivabradine of formula (II):

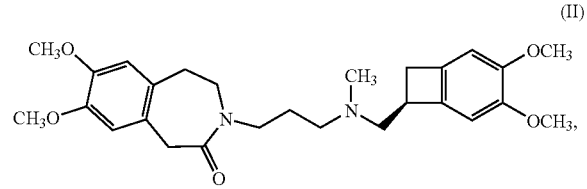

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also of various pathologies involving rhythm disturbances, especially supraventricular rhythm disturbances.

DESCRIPTION OF THE PRIOR ART

The preparation and therapeutic use of ivabradine and addition salts thereof with a pharmaceutically acceptable acid, and more especially its hydrochloride, have been described in the European patent specification EP 0 534 859.

That patent specification describes the synthesis of ivabradine hydrochloride by reacting the compound of formula (III):

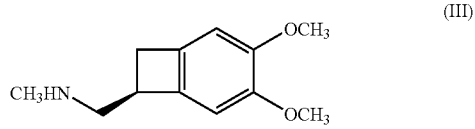

with the compound of formula (IV)

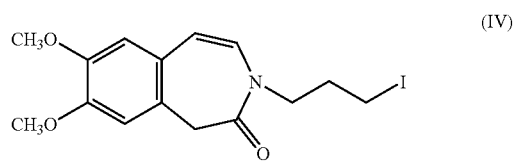

to yield the compound of formula (V):

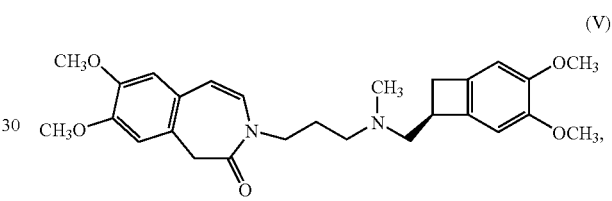

the catalytic hydrogenation of which yields ivabradine, which is then converted into its hydrochloride.

That method has the disadvantage of yielding ivabradine hydrochloride in only a very low yield—less than 17% over the 3 steps as a whole.

That very low yield is due in part to the mediocre yield of the step of catalytic hydrogenation of the 1,3-dihydro-2H-3-benzazepin-2-one function of the compound of formula (V) into the corresponding 1,3,4,5-tetrahydro-2H-3-benzazepin-2-one.

Under the conditions employed (hydrogenation catalysed using 10% palladium hydroxide, at ambient temperature, in glacial acetic acid), the yield of that reduction reaction is in fact only 40%.

In view of the pharmaceutical value of ivabradine and its salts, it has been imperative to be able to obtain the 1,3,4,5-tetrahydro-2H-3-benzazepin-2-one compound of formula (I) by an effective industrial process, and especially in a good yield.

Considering the mediocre yield described in EP 0 534 859 for reduction of the 1,3-dihydro-2H-3-benzazepin-2-one function, it seemed that catalytic hydrogenation would not be able to meet such a set of requirements.

Nevertheless, the Applicant has found, surprisingly, that selection of very specific reaction conditions, especially solvent, allows the 1,3,4,5-tetrahydro-2H-3-benzazepin-2-one compound of formula (I) to be obtained in a very good yield by catalytic hydrogenation of the corresponding 1,3-dihydro-2H-3-benzazepin-2-one.

DETAILED DESCRIPTION OF THE INVENTION

More specifically, the present invention relates to a process for the synthesis of compounds of formula (I):

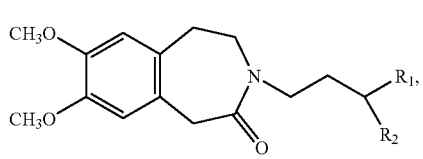

wherein $R_1$ and $R_2$, which may be the same or different, each represent a linear or branched ($C_1$–$C_8$)alkoxy group or form, together with the carbon atom carrying them, a 1,3-dioxane, 1,3-dioxolane or 1,3-dioxepane ring, which process is characterised in that the compound of formula (VI):

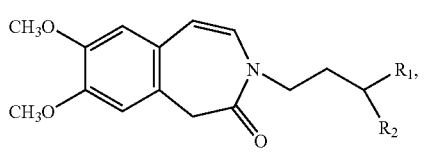

wherein $R_1$ and $R_2$ are as defined hereinbefore,
is subjected to a catalytic hydrogenation reaction,
in a non-acidic solvent,
and then the reaction mixture is filtered
to yield the compound of formula (I).

Among the preferred non-acidic solvents which can be used for the process of the invention, there may be mentioned, without implying any limitation, acetates, alcohols, preferably ethanol, methanol or isopropanol, tetrahydrofurane, toluene, dichloromethane and xylene.

Among the catalysts that can be used for the process of the invention, there may be mentioned, without implying any limitation, palladium, platinum, nickel, ruthenium, rhodium, and their compounds, particularly in supported form or in oxide form. A preferred catalyst is palladium-on-carbon.

The temperature of the hydrogenation reaction is preferably from 20 to 100° C., more preferably from 40 to 80° C., even more preferably from 45 to 65° C.

The hydrogen pressure during the hydrogenation reaction of the compound of formula (VI) is preferably from 1 to 220 bars, more preferably from 1 to 100 bars, even more preferably from 1 to 30 bars.

In the process according to the invention, the compounds of formula (VI) preferably used are the compounds of formula (VIa), which are particular cases of the compounds of formula (VI) wherein $R_1$ and $R_2$ form, together with the carbon atom carrying them, a 1,3-dioxane, 1,3-dioxolane or 1,3-dioxepane ring.

The compounds of formula (I) are new products which are useful as synthesis intermediates in the chemical or pharmaceutical industry, especially in the synthesis of ivabradine and addition salts thereof with a pharmaceutically acceptable acid, and as such they form an integral part of the present invention.

By way of example, deprotection of the diacetal of formula (I) yields the aldehyde of formula (VII):

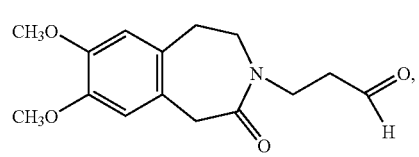

which is reacted with (7S)-3,4-dimethoxybicyclo[4.2.0]octa-1,3,5-trien-7-yl]-N-methylmethanamine under conditions of reductive amination to yield ivabradine.

The preferred compounds of formula (I) are those wherein $R_1$ and $R_2$ form, together with the carbon atom carrying them, a 1,3-dioxane, 1,3-dioxolane or 1,3-dioxepane ring.

The Example hereinbelow illustrates the invention.

EXAMPLE

3-[2-(1,3-Dioxolan-2-yl)-ethyl]-7,8-dimethoxy-1,3,4,5-tetrahydro-2H-3-benzazepin-2-one Introduce 100 g of 3-[2-(1,3-dioxolan-2-yl)-ethyl]-7,8-dimethoxy-1,3-dihydro-2H-3-benzazepin-2-one, 500 ml of isopropanol and 10 g of Pd/C into a hydrogenator. Purge with nitrogen and then with hydrogen, heat to 60° C., and then hydrogenate at that temperature under a pressure of 1 bar for 4 hours.

Filter the reaction mixture at 60° C. in order to remove the catalyst.

Rinse with 2×50 ml of isopropanol.

Cool to 50° C. and add 200 ml of tert-butyl methyl ether (MTBE).

Cool to 20° C. and then chill at 5° C. for 1 hour 0 minutes.

Filter off the crystals obtained at 5° C. Dry to constant weight.

The expected compound is obtained in a yield of 88% and with a chemical purity greater than 98%.

We claim:
1. A process for the synthesis of compounds of formula (I):

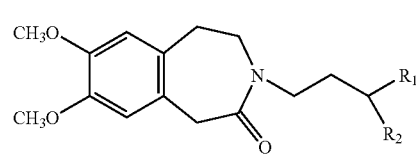

wherein $R_1$ and $R_2$, which may be the same or different,
each represent linear or branched ($C_1$–$C_8$)alkoxy or form, together with the carbon atom carrying them, a 1,3-dioxane, 1,3-dioxolane or 1,3-dioxepane ring, wherein a compound of formula (VI):

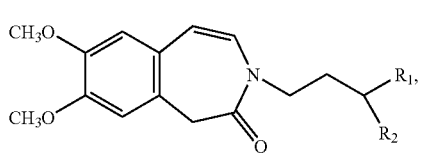

(VI)

is subjected to a catalytic hydrogenation reaction, in a non-acidic solvent, and then the reaction mixture is filtered to yield the compound of formula (I).

2. The process of claim 1, wherein the catalyst for the hydrogenation reaction of the compound of formula (VI) is palladium-on-carbon.

3. The process of claim 1, wherein the hydrogen pressure during the hydrogenation reaction of the compound of formula (VI) is from 1 to 220 bars.

4. The process of claim 1, wherein the hydrogenation reaction of the compound of formula (VI) is carried out in an alcoholic solvent.

5. The process of claim 4, wherein the alcoholic solvent is ethanol, methanol or isopropanol.

6. The process of claim 1, wherein the temperature is from 20 to 100° C.

7. The process of claim 6, wherein the temperature is from 40 to 80° C.

8. The process of claim 1, wherein $R_1$ and $R_2$ form, together with the carbon atom carrying them, a 1,3-dioxane, 1,3-dioxolane or 1,3-dioxepane ring.

9. A compound selected from those of formula (I):

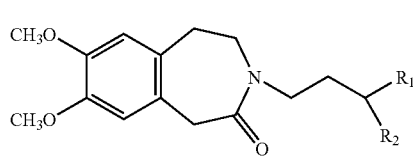

(I)

wherein $R_1$ and $R_2$, which may be the same or different, each represent linear or branched ($C_1$–$C_8$)alkoxy or form, together with the carbon atom carrying them, a 1,3-dioxane, 1,3-dioxolane or 1,3-dioxepane ring.

10. The compound of claim 9, wherein $R_1$ and $R_2$ form, together with the carbon atom carrying them, a 1,3-dioxane, 1,3-dioxolane or 1,3-dioxepane ring.

11. A process for the synthesis of ivabradine, pharmaceutically acceptable salts thereof and hydrates thereof, starting from a compound of formula (I), wherein the compound of formula (I) is obtained according to the process of claim 1, wherein the compound of formula (I) is subjected to deprotection conditions to yield an aldehyde of formula (VII):

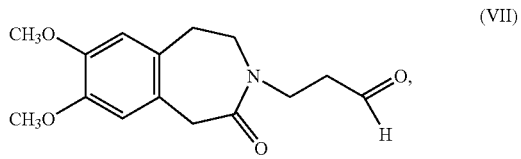

(VII)

which is reacted with (7S)-3,4-dimethoxybicyclo[4.2.0]octa-1,3,5-trien-7-yl]-N-methylmethanamine under reductive amination conditions to yield ivabradine, which is converted, if desired, into a pharmaceutically acceptable salt or hydrate.

* * * * *